United States Patent [19]

Rase et al.

[11] Patent Number: 5,169,631
[45] Date of Patent: Dec. 8, 1992

[54] TOPICAL ANTIMICROBIAL COMPOSITION AND USES

[75] Inventors: Didier Rase, Paris; Ali Salhi, Saint Gely du Fesc, both of France

[73] Assignee: Laboratories Care System, Boulogne Billancourt, France

[21] Appl. No.: 595,286

[22] Filed: Oct. 10, 1990

[30] Foreign Application Priority Data

Oct. 10, 1989 [FR] France ................. 89 13212

[51] Int. Cl.$^5$ ..................... A61K 7/32; A61K 9/50
[52] U.S. Cl. ..................... 424/401; 424/408; 424/451; 424/452; 424/65; 424/489
[58] Field of Search .......... 424/489, 490, 491, 493, 424/499, 409, 47, 61, 65, 401, 408, 451, 452; 530/356

[56] References Cited

U.S. PATENT DOCUMENTS

| | | | |
|---|---|---|---|
| 4,280,954 | 7/1981 | Yannas et al. | 260/123.7 |
| 4,350,629 | 9/1982 | Yannas et al. | 260/123.7 |
| 4,448,718 | 5/1984 | Yannas et al. | 260/123.7 |
| 4,666,641 | 5/1987 | Fickat et al. | 264/4.3 |
| 4,780,321 | 10/1988 | Levy et al. | 424/499 |
| 4,801,458 | 1/1989 | Hidaka et al. | 424/443 |
| 4,853,224 | 8/1989 | Wong | 424/427 |
| 4,978,352 | 12/1990 | Fedorov et al. | 606/166 |

FOREIGN PATENT DOCUMENTS 0381543 8/1990 European Pat. Off. .

OTHER PUBLICATIONS

Chemical Abstracts, vol. 112, No. 24, Jun. 11, 1990, 223, 263v, p. 414.
Chemical Abstracts, vol. 112, No. 2, Jan. 8, 1990, 8515y, p. 45.

*Primary Examiner*—Thurman K. Page
*Attorney, Agent, or Firm*—Wegner, Cantor, Mueller & Player

[57] ABSTRACT

The present invention relates to a topical antimicrobial composition, comprising microcapsules containing an antimicrobial agent, wherein the wall of the said microcapsules is formed of collagen and glycosaminoglycan cross-linked by means of a cross-linking agent. The antimicrobial composition of the invention may be used in body deodorants and in topical disinfectants.

13 Claims, No Drawings

TOPICAL ANTIMICROBIAL COMPOSITION AND USES

The present invention relates to deodorant antiseptic compositions to be applied to the skin, with a sustained and adjustable activity and which contain an antimicrobial agent enclosed in microcapsules, the wall of which is constituted of cross-linked collagen and glycosaminoglycan.

It is known that the skin flora is very varied, aerobic or anaerobic, composed in particular of *Staphylococcus epidermus, Staphylococcus aureus* and other micrococci, aerobic corynebacteriae, enterobacteriae such as *Escherichia coli*, Klebsiella, Proteus or propionobacteriae, in relative amounts which depend on the anatomical location as mentioned, for example, by J. Fleurette in the Revue du Practicien—30(51) p. 3471–3480 (1980).

Moreover, it has been shown that the odor of perspiration, in particular that of the armpits, is due to the action of microorganisms on sweat, since this latter does not contain malodorous compounds at the time of its secretion. Reference may be made, for example, to the articles by J. J. Leyden et al. in the J. of Investigative Dermatology 77, 413–416 (1981), by J. N. Labows in J. Soc. Cosm. Chem. 33, 193–202 (7/1982) or Seminars in Dermatology 1 (2) 143–148 which study the nature of the microorganisms causing the unpleasant odors of perspirations. Gram- bacteriae and propiono-bacteria are hardly implicated at all in these odors, whereas corynebacteria and other aerobic diphtheroid bacilli are always associated with them, as well as micrococci to a lesser degree.

Consequently, antimicrobial agents, which suppress the formation of the malodorous products resulting from the decomposition of sweat by inhibiting bacterial growth, are now usually incorporated into body deodorant compositions.

The use of antimicrobial agents in dermatology and in body hygiene is also necessary.

Besides, it is known that the microencapsulation of pharmaceutical and cosmetic active ingredients in water-soluble or biodegradable polymer-based membranes is frequently used to increase the stability of the product, to mask an odor or a taste, or also in order to prolong the duration of action of the composition.

The microcapsules according to the invention release their active ingredient essentially in the presence of the microorganisms of the skin which is has to control. In fact, the wall of the microcapsules is altered by the action of the proteolytic enzymes secreted by the skin flora.

The compositions according to the invention thus are useful in deodorant compositions with sustained activity.

In addition, they are useful in cutaneous antiseptic compositions with a sustained activity which can be applied to superficial wounds or mild burns.

Thus, a subject matter of this invention are topical antimicrobial compositions comprising microcapsules containing an antimicrobial agent, wherein the wall of said microcapsules in constituted of collagen and glycosaminoglycan cross-linked by means of a cross-linking agent.

The wall of the microcapsules is constituted essentially of collagen, and more particularly atelocollagen, and of a natural glycosaminoglycan, such as chondroitin sulfates, mucopolysaccharides extracted from the nasal septum of the sheep, dermatan sulfates or heparan sulfate.

Atelocollagen is a collagen become partially uncross-linked by enzymatic treatment as described in patent application FR-A-2 622 104; this more soluble collagen no longer bears telopeptide ends.

The cross-linking agent is preferably an acid dichloride, for example sebacoyl dichloride, terephthaloyl dichloride and adipoyl dichloride, or a diisocyanate, for example tolyldiisocyanate.

Of the antimicrobial agents commonly used to maintain cutaneous antisepsis, compounds practically insoluble in water which are incorporated in microcapsules in the form of an oily solution or suspension are preferred. Among suitable antimicrobial agents mention may be made of carbanilides—such as cloflucarban, triclocarban-, phenols—such as hexachlorophenol, triclosan and parabens-, nitrofurans—such as nitrofurazone-, imidazoles —such as clotrimazole and miconazole-, or undecylenic acid and its esters.

The oil may be a vegetable oil, such as castor oil, a fatty acid ester, such as a triester of glycerol, for examples a triglyceride of caprylic and capric acids, a glycol diester, for example the propyleneglycol dilaurate or also a fatty acid ester or fatty alcohol ester, for example isopropyl myristate and amyl acetate.

The microcapsules according to the invention can be prepared by a known method, that is interfacial polymerization. The oily phase containing the active ingredient and the dissolved cross-linking agent, is poured with stirring into the aqueous solution of collagen and glycosaminoglycan, in the presence of a base such that the pH is maintained between 7 and 10.

The density and thickness of the walls of the microcapsules vary with the concentration of the cross-linking agent in the medium. Usually, acid chlorides are used at a concentration of 2 g to about 10 g/100 g of oily phase containing the active ingredient; if the concentration is too low, the microcapsules are porous; the man skilled in the art is able to determine the appropriate concentration after some preliminary tests. The concentration of the active ingredient in the oily phase is conditioned by its intrinsic activity and its solubility; it is preferably from 10% to 60% by weight. The microcapsules formed are separated by centrifugation or filtration and are washed with water.

They are preferably stored in suspension in water, where appropriate in the presence of a preservative if they are not used promptly for the preparation of antiseptic or deodorant compositions according to the invention.

The deodorant compositions according to the invention, for application in particular to the armpits or the feet, may be in the form of sticks, gels or powders or packaged in roll-on applicators or in sprays; they contain from 0.1 to 2% by weight of microcapsules, depending on the antimicrobial agent used.

The compositions of the invention for cutaneous antisepsis are preferably in the form of a cream or, better still, a spray; they contain from 0.5 to 3% by weight of microcapsules.

In order to obtain an immediate effect, it is also possible to introduce into the antiseptic and deodorant compositions a small amount of a free antimicrobial agent, identical or not with the one present in the microcapsules.

For incorporation into compositions to be packaged in pressure sprays, it is preferable that the microcapsules have a diameter of 10 μm, but they may be up to 50 μm in diameter without risk of blocking the valve of the spray and in case of gel, cream, stick or other forms, microcapsules may be used having a diameter of up to 100 μm.

The compositions according to the invention are prepared in a known manner with conventional excipients. These compositions are essentially water-based in order that, during storage, there is no progressive extraction of the content of the microcapsules by a solvent of the oil and/or antimicrobial agent.

In what follows, several examples of deodorant compositions according to the invention are described as well as the results obtained with these compositions.

PREPARATION AND STUD OF MICROCAPSULES a) Preparation

In an homogenizer of the Ultra Turax ®type rotating at 6000 rev/minute 40 g of triclosan are mixed with 60 g of triglycerides of caprylic and capric acids, marketed by Henkel under the catalogue name of Myritol ®318, which is available in the form of a neutral oil of low viscosity (about 30 mPa.s at 20° C). 5 ml of sebacoyl chloride are then added and the mixture is poured with stirring into an aqueous solution consisting of 4.8 g of atelocollagen, 1.8 g of chondroitin 4-sulfate, 14.4 g of sodium carbonate ($Na_2CO_3$) and 300 ml of water; the initial pH of the aqueous phase if 9.8; stirring is carried out by means of a planetary stirrer rotating at 600 rev/-minute; it is maintained for 1 hour before the addition of an equal volume of water to the mixture from the medium by centrifugation at 2000 rev/min.

After two washings with 150 ml of water, the final centrifugation pellet, which in the moist state weighs about 160 g, is suspended in water at a concentration of 10 g/100 ml, together with Phenonip ® at a concentration of 0.5 g/100 ml (test A), if necessary; the Phenonip is a preservative consisting of a 30% solution in 2-phenoxyethanol of a mixture of methyl to butyl esters of p-hydroxybenzoic acid.

Other tests were carried out under the same conditions, except that only 2 ml (test B) or 3 ml (tests C) of acid chloride were used.

The microcapsules thus prepared have a diameter varying between 1 and 10 μm and contain about 40% of triclosan by weight; they are not altered in acidic medium nor by heating to 100° C. for 10 minutes.

b) Study of the degradation of the microcapsules

A 5 g/100 ml suspension of microcapsules was placed in contact for 24 hours with either collagenase type II, extracted from *Clostridium histolyticum*, at 37° C. and pH 7.6 at a concentration of 1000 U/ml, or with a 24 hour culture of a bacterial suspension in a ratio of 1 volume of suspension of microcapsules of 10 g/100 ml to 9 volumes of culture. The bacteria studied were *Staphylococcus aureus, Enterobacter cloacae, Serratia marcescens* and *Proteus vulgaris*.

The microcapsules were observed before and after contact with the Leitz Dialux microscope fitted with a camera enabling characteristic features to be photographed. Suspensions of 10 g/100 ml of microcapsules, containing oil but no antimicrobial agent, in water containing 0.5 g/100 ml of preservative were also observed.

All of the microcapsules placed in contact with collagenase burst and only oily droplets were observed in the medium. The action of the bacteria was varied; depending on the state of cross-linking of the wall and the bacteria a thinning of the walls, their rupture with release of the content by opening and deformation of the capsule or their disaggregation were observed; some microcapsules were not modified but sometimes the bacteria adhered to the walls, forming small swellings. The attack on the walls was prononced with *E. cloacae* and *P. vulgaris*.

c) Study of antibacterial activity

Two bacterial strains, *E. clocae* and *P. vulgaris* were placed in contact with the microcapules of test A; a preservative control, i.e. 0.5% aqueous solution of Phenonip and a control composed of a bacterial inoculum in nutrient broth were also studied. The results of these tests are reported in table I below; they show that in the case of the microcapsules there is a decrease of 5 to 6 decimal logarithms of the number of bacteria after 6 hours compared to the beginning whereas after 24 hours there are not surviving bacteria; this clearly reflects a progressive release of the active ingredient.

TABLE I

| Strain | Preparation | Number of bacteria surviving at the times of contact indicated (h) | | |
|---|---|---|---|---|
| | | 0 | 6 | 24 |
| Enterobacter cloacae | Test A | $8,4 \times 10^8$ | $5,7 \times 10^3$ | $<10$ |
| | Preservative control | $1,2 \times 10^9$ | $3,7 \times 10^9$ | $2 \times 10^9$ |
| | Inoculum control | $1,2 \times 10^9$ | $3,3 \times 10^9$ | $4 \times 10^9$ |
| Proteus | Test A | $3,3 \times 10^8$ | $4 \times 10^2$ | $<10$ |
| | Preservative control | $2,9 \times 10^8$ | $2,3 \times 10^9$ | $1 \times 10^{10}$ |
| | Inoculum control | $2,9 \times 10^8$ | $6,5 \times 10^9$ | $1,9 \times 10^{10}$ |

Some example of the compositions according to the invention will be given below.

EXAMPLE 1

A bacterial gel having the following composition, is prepared according to usual method:

| carboxypolymethylene (Carbopol 940) | 0.4 g |
|---|---|
| water-soluble silicones | 20 g |
| triclosan | 0.15 g |
| microcapsules from test A | 3 g |
| triethanolamine | 0.3 g |
| water to | 100 ml |

EXAMPLE 2

A feet powder is prepared which contains the following ingredients:

| keto-stearyl alcohol | 2 g |
|---|---|
| 2-octyl dodecanol | 2 g |
| zinc stearate | 10 g |
| glycerol mono-undecylenate | 5 g |
| microcapsules from test A | 3 g |
| piroctone (ethanolamine salt) | 0.2 g |
| polyamine-12 (Orgasol ® Atochem) | 20 g |
| perfume | 0.2 g |
| talc to | 100 g |

EXAMPLE 3

A suspension having the following composition is prepared and is introduced into bottles fitted with a spraying pump:

| | |
|---|---|
| polydimethylcyclosiloxane (Cyclomethicone)* | 50 g |
| Cyclomethicone and dimethicone* copolyol (Dow Corning) | 25 g |
| Pareth 1,5-3*# | 1.5 g |
| triclosan | 0.15 g |
| glycyrrhetinic acid | 1.5 g |
| microcapsules from test A | 3 g |
| perfume | 0.5 g |
| water to | 100 ml |

*name given by CFTA (Cosmetic Toiletories and Fragance Association)
ether of polyethyleneglycol and $C_{11}$ to $C_{14}$ fatty alcohols

EXAMPLE 4

A suspension having the following composition is prepared and introduced with a propellant gas into an aerosol spray:

| | |
|---|---|
| PEG-7 and glyceryl cocoate* | 7 g |
| glycyrrhetinic acid | 1.5 g |
| vaseline oil | 40 g |
| microcapsules from test B | 5 g |
| Cyclomethicone* | 45.5 g |
| perfume | 1 g |

EXAMPLE 5

A deodorant stick without alcohol and having the following composition is prepared according to usual method:

| | |
|---|---|
| Cyclomethicone* | 24 g |
| Cyclomethicone* and Dimethicone* copolyol | 24 g |
| Pareth* 15-3 | 1.5 g |
| Microcrystalline wax of branched hydrocarbons | 13 g |
| phytosterols | 6 g |
| triclosan | 0.15 g |
| microcapsules from test A | 3 g |
| glycyrrhetinic acid | 1.5 g |
| perfume | 0.2 g |

-continued

| | |
|---|---|
| $H_2O$ | 26.65 g |

We claim:

1. A topical antimicrobial composition with sustained activity comprising microcapsules containing an antimicrobial agent to maintain cutaneous antisepsis, wherein the wall of said microcapsules is constituted of collagen and glycosaminoglycan cross-linked by means of a cross-linking agent.

2. Antimicrobial composition according to claim 1, wherein the collagen is atelocollagen.

3. Antimicrobial composition according to claim 1, wherein the glycosaminoglycan is selected from chondroitin 4-sulfates, dermatan sulfates and heparan sulfates.

4. Antimicrobial composition according to claim 2, wherein the glycosaminoglycan is selected from chondroitin 4-sulfates, dermatan sulfates and heparan sulfates.

5. Antimicrobial composition according to claim 1, wherein the cross-linking agent is an acid dichloride.

6. Antimicrobial composition according to claim 1, wherein the cross-linking agent is sebacoyl dichloride.

7. Antimicrobial composition according to claim 1, wherein the microcapsules contain an oil and an antimicrobial agent insoluble in water.

8. Antimicrobial composition according to claim 7, wherein the oil is a fatty acid ester.

9. Antimicrobial composition according to claim 1, wherein the microcapsules contain triclosan and triglyceride of caprylic and capric acids.

10. A topical deodorant comprising an effective amount of a composition as claimed in claim 1.

11. A skin deodorant composition comprising an effective deodorizing amount of a composition as claimed in claim 2.

12. A topical disinfectant comprising an effective antimicrobial amount of a composition as claimed in claim 1.

13. A topical disinfectant comprising an effective antimicrobial amount of a composition as claimed in claim 2.

* * * * *